United States Patent [19]

Kühnert et al.

[11] Patent Number: 5,456,935
[45] Date of Patent: Oct. 10, 1995

[54] FOOD PRODUCTS

[75] Inventors: Manfred Kühnert, Leipzig; Anton F. Haase, Muhltal; Hans W. Kleffner, Battenberg, all of Germany

[73] Assignee: Rutgerswerke AG, Germany

[21] Appl. No.: 340,255

[22] Filed: Nov. 16, 1994

[30] Foreign Application Priority Data

Nov. 27, 1993 [DE] Germany .......................... 43 40 485.5

[51] Int. Cl.⁶ .................................................. A21D 10/00
[52] U.S. Cl. ................................................................ 426/549
[58] Field of Search ............................................... 426/549

[56] References Cited

U.S. PATENT DOCUMENTS

| | | |
|---|---|---|
| 4,918,059 | 4/1990 | Seubert et al. . |
| 4,921,840 | 5/1990 | Seubert et al. . |
| 4,946,829 | 8/1990 | Seubert et al. . |
| 5,034,045 | 7/1991 | Alexander ............................ 71/24 |
| 5,284,651 | 2/1994 | Riede et al. . |
| 5,360,915 | 11/1994 | Riede et al. . |

OTHER PUBLICATIONS

European Search Report No. 94 11 3103; Database WPI, Section Ch, Week 7631 Derwent Publications Ltd., London, GB; Class C03, AN76–59132X & JP–B–51 022050. (Mitsui Toatsu Cheml Inc.) (Jul. 8, 1976).

Webster's Third New International Dictionary (1961) p. 664.

Primary Examiner—Jeanette Hunter
Assistant Examiner—Choon P. Koh
Attorney, Agent, or Firm—Bierman and Muserlian

[57] ABSTRACT

A food product containing an effective amount of a water-soluble alkali metal or ammonium huminate with a molecular weight of up to 50,000 D produced synthetically by oxidation of multi-valent phenolic compounds sufficient to protect the gastric and intestinal regions of a warm-blooded animal.

4 Claims, No Drawings

5,456,935

FOOD PRODUCTS

STATE OF THE ART

It is known that humic matter has an anti-inflammatory and detoxifying effect in the gastric and intestinal tract and therefore, animal pharmaceuticals and such to be administered with food are sold under the marks Dystikum, Sulumin and Humocarb, which comprise a mixture of various natural huminates having molecular weights up to 100,000 as the effective component. These agents are non-toxic when taken orally and no undesirable side-effects have been observed even following long-term administration. Moreover, no toxic degradation products are formed and the substances excreted again can be viewed as natural products which do not represent any harm to the environment.

But the products have the grave disadvantage in that the humic matter has only a passing effect, i.e. these substances act only on the particular gastric and intestinal mucosa while the food bolus passes through this region. Such mechanism of action is undesirable in the case of substances which are to be used in the field of human therapy since it is impossible for a human being to eat continuously or to consume the same food at all times.

OBJECTS OF THE INVENTION

It is an object to provide novel food products capable of protecting the gastric and intestinal systems of warm-blooded animals and a method of protecting the warm-blooded animals.

These and other objects and advantages of the invention will become obvious from the following detailed description.

THE INVENTION

The novel food products of the invention contain an effective amount of a water-soluble alkali metal or ammonium huminate with a molecular weight of up to 50,000 D produced synthetically by oxidation of multivalent phenolic compounds sufficient to protect the gastric and intestinal regions of a warm-blooded animal.

The invention solves the problem of providing substances having at least equally good effectiveness in the gastric and intestinal region as the known natural humic substances with respect to their toxicity, side-effects and environmental harm corresponding to the natural humic substances, yet whose duration of effectiveness is significantly extended so that even after they have passed the gastrointestinal tract, a corresponding pharmacological efficacy is retained.

This invention provides industrially prepared foods used for human nutrition by using water-soluble alkali metal or ammonium huminates having a molecular weight of up to 50,000 D, produced synthetically through oxidation of multivalent phenolic compounds for dietary products.

It was found that these synthetic, relatively low-molecular weight, water-soluble alkali metal or ammonium huminates when administered orally have an anti-inflammatory and detoxifying effect in the gastric and intestinal region. However, in contrast to the huminates used previously in pharmaceutical agents administered with food or as food or feed additives, they are absorbed and stored in the region of the intestinal mucosa and have an approximately constant effect over an extended period of time even if the food bolus containing them has long passed the intestine, i.e. these huminates used according to the invention exhibit marked sustained action.

Inflammations of the intestinal mucosa subside more rapidly and viruses and bacterial organisms are inactivated to a greater degree. The natural intestinal flora of microorganisms is not disturbed but, surprisingly, is stabilized. Digestive problems occurring frequently due to changing nutrition and climates, especially when travelling in remote countries, are not observed when these huminates are taken simultaneously.

The water-soluble alkali metal or ammonium huminates having a molecular weight of up to 50,000 D and produced synthetically through oxidation of multivalent phenolic compounds can be used for the production of food products and are observed to have additional, to some extent surprising, advantages: namely, the huminates of the invention exhibit a strong vermifugal effect in animal experiments. After regular administration of these huminates over a period of approximately eight days, the treated animals, without exception, were free of worms. This applies particularly in the case of cestodes. It should be expected that such effect is also attained in humans if the huminates are consumed in the form of food products.

Huminates have a detoxifying effect and this applies with respect to heavy metals which might potentially be taken up as well as with respect to toxic protein substances formed by foreign organisms in the intestinal region.

Although the huminates are absorbed on the intestinal mucosa, they are not incorporated into the body. This means that these huminates act locally and the liver and kidney are not stressed through degradation processes or products due to the huminates. A further practical advantage of the huminates used resides therein that they are completely water-soluble and therefore permit a multiplicity of simple possibilities for preparing appropriate food products.

The food products of the invention comprise water-soluble alkali metal or ammonium huminates with a molecular weight of up to 50,000 D and produced synthetically through oxidation of multivalent phenolic compounds. The quantity of huminate can vary over a wide range and depends also on the quantity of the food product consumed in each instance. The concentration is generally in the range of 0.05 to 5% by weight. It should be adjusted so that with the consumption of the food product of the invention, approximately an amount of 0.005 to 0.5 g of huminate is ingested per kg of body weight per day.

In the simplest case, the food products of the invention exist in liquid form, i.e. they are aqueous solutions of the huminates. 0.05 to 1% solutions of this type can moreover include flavoring agents or sweeteners, mineral or other substances contributing to building-up the body, are used as drinks.

The food products of the invention in the form of concentrated solutions can be added to food seasonings if the brown color does not bother the eater and the seasoning is not heated after it is added to the food. The analogous condition applies also, if the food products are present in pasty form, i.e. if aqueous solutions of the huminates are either combined with a filler substance and/or are emulsified with an oil or fat.

Appropriate filler substances can be either inert inorganic materials such as silicates or heavy spar or natural organic materials, particularly cellulose-containing materials such as wheat bran, carob meal or ground husks.

The food products of the invention can also be present in solid form, possibly raw fruit and vegetable products mixed with huminates or baked goods containing huminates. The latter are particularly small baked goods such as sponge cakes or cookies which can readily be baked by heating them briefly. For their production, 0.1 to 2% by weight of huminate are added to a dough known per se such as is conventionally used for such products, either as a solid substance or as a solution and mixed with it. After shaping this substance, it is baked by being heated briefly.

Surprisingly, it was found that by raising the temperature rapidly to 150° to 180° C. and short baking times (up to 2 minutes), a sufficient baking effect is attained, but the huminates are not markedly broken down or otherwise damaged in the process. A particularly careful baking process is a microwave treatment in which the microwaves are introduced for 10 to 30 seconds with an intensity which allows the formed dough substance to be baked.

Huminates which can be used and which are effective are low-molecular weight, ammonium or alkali metal huminates produced synthetically through oxidation and the resulting polycondensation of multivalent phenols in a weakly alkaline aqueous medium as described in U.S. Pat. No. 4,921, 840. They are dark-brown, water-soluble products with an average molecular weight of 1000 with a spread from 250 to 1500. Their aqueous solutions do not exhibit any Tyndall effect and they do not fluoresce.

But also effective are synthetic huminates having molecular weights of up to 50,000 D, if they have the following characteristics: They have a positive physiologic effect, i.e. they have healing properties, have very low toxicity or embryotoxicity and are neither mutagenic nor teratogenic and also not carcinogenic. Their aqueous solutions do not exhibit any Tyndall effect and they do not fluoresce. Appropriate tests of these properties are usefully performed using aqueous solutions at a concentration such that they retain approximately 50% of the transmission of irradiated light. Examples of appropriate synthetic huminates are products produced in U.S. Pat. No. 5,284,651.

Also usable are modified ammonium or alkali metal huminates such as are known from U.S. Pat. No. 5,360,915 where they are produced by oxidation of compounds having the formulae

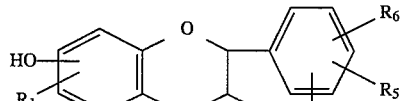

and/or

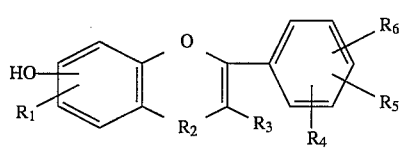

wherein $R_1$, $R_3$ and $R_4$ are individually OH or hydrogen, $R_2$ is CO or $CH_2$ and $R_5$ and $R_6$ are individually hydrogen, OH or methoxy in alkaline aqueous solutions (pH 9).

The compounds of formulae I and II can be used as single pure substances as well as in any mixture. They can also be used in a reaction mixture with multivalent phenols which for economic reasons can be quite appropriate.

In the following examples, there are described several preferred embodiments to illustrate the invention. However, it is to be understood that the invention is not intended to be limited to the specific embodiments.

EXAMPLE 1

A dough substance was prepared by mixing flour, fat, sugar, hazelnuts, eggs, baking powder, spices, and water. A portion of the water was an aqueous solution of sodium huminate with an average molecular weight of 1000 with a spread from 300 to 1500 and produced by oxidation of hydroquinone according to the example of U.S. Pat. No. 4,921,840. The quantity of huminate was such that the resulting dough substance had a sodium huminate content of 1% by weight. The dough was formed into cookies which were briefly heated to 170° C. in a continuous oven and held for 1 minute at this temperature. The baked cookies were somewhat darker and sweeter than comparison cookies produced from an analogous dough without huminates. Otherwise, no difference in taste or smell could be detected.

EXAMPLE 2

One half of the participants of a group travelling in a country with a diminished standard of hygiene ate daily per person for 7 days before and during the trip 5 cookies of Example 1. The travelers had no digestive problems during their travel while 60% of the remaining travelers in this group (control group) suffered from diarrhea after a few days.

Various modifications of the compositions or method of the invention may be made without departing from the spirit or scope thereof and it is to be understood that the invention is intended to be limited only as defined in the appended claims.

What we claim is:

1. A baked goods product containing an effective amount of a water-soluble alkali metal or ammonium huminate with a molecular weight of up to 50,000 D produced synthetically by oxidation of multivalent phenolic compounds sufficient to protect the gastric and intestinal regions of a human.

2. A process for the preparation of baked goods of claim 1 comprising forming a flour dough containing 0.1 to 2% by weight of an alkali metal or ammonium huminate with a molecular weight of up to 50,000 D produced by oxidation of multivalent phenolic compounds, shaping the dough and baking by heating for a short period of time whereby the huminates are not broken down or otherwise damaged in the process.

3. The process of claim 2 wherein the baking is effected by a microwave treatment for 10 to 30 seconds.

4. A method of protecting the gastric and intestinal systems of humans from infection comprising feeding the humans a food product of claim 1.

* * * * *